United States Patent
Schaller et al.

(10) Patent No.: US 6,641,593 B1
(45) Date of Patent: Nov. 4, 2003

(54) TISSUE CONNECTOR APPARATUS AND METHODS

(75) Inventors: Laurent Schaller, Los Altos, CA (US); Charles T. Maroney, Portola Valley, CA (US); Phillip Drews, San Jose, CA (US); Isidro Matias Gandionco, Fremont, CA (US); John Nguyen, San Jose, CA (US)

(73) Assignee: Coalescent Surgical, Inc., Sunnyvale, CA (US)

( * ) Notice: Subject to any disclaimer, the term of this patent is extended or adjusted under 35 U.S.C. 154(b) by 0 days.

(21) Appl. No.: 09/090,305

(22) Filed: Jun. 3, 1998

(51) Int. Cl.[7] ............................................. A61B 17/08
(52) U.S. Cl. ....................................... 606/157; 606/222
(58) Field of Search ................................ 606/154, 153, 606/222, 223, 216, 78, 215; 29/243.5, 243.56

(56) References Cited

U.S. PATENT DOCUMENTS

| 43,098 A | 6/1864 | Cooper |
| 655,190 A | 8/1900 | Bramson |
| 1,583,271 A | 5/1926 | Biro |
| 1,625,602 A | 4/1927 | Gould et al. |
| 2,240,330 A | 4/1941 | Flagg et al. ................. 128/339 |
| 2,256,382 A | 9/1941 | Dole ............................ 1/49.1 |
| 2,264,679 A | 12/1941 | Ravel ........................ 128/340 |
| 2,516,710 A | 7/1950 | Mascolo |
| 2,715,486 A | 8/1955 | Marcoff-Moghadam et al. ............................ 223/102 |
| 2,890,519 A | 6/1959 | Storz, Jr. ..................... 29/225 |
| 3,249,104 A | 5/1966 | Hohnstein |
| 3,274,658 A | 9/1966 | Pile .............................. 24/259 |
| 3,452,742 A | 7/1969 | Muller .......................... 128/2 |
| 3,506,012 A | 4/1970 | Brown ........................ 128/346 |
| 3,509,882 A | 5/1970 | Blake ......................... 128/325 |
| 3,547,103 A | 12/1970 | Cook ......................... 128/2.05 |
| 3,570,497 A | 3/1971 | Lemole ................... 128/335.5 |
| 3,608,095 A | 9/1971 | Barry |
| 3,638,654 A | 2/1972 | Akuba ........................ 128/340 |
| RE27,391 E | 6/1972 | Merser |
| 3,753,438 A | 8/1973 | Wood et al. ................. 128/335 |
| 3,875,648 A | 4/1975 | Bone ............................ 29/417 |
| 3,910,281 A | 10/1975 | Kletschka et al. .......... 128/335 |
| 3,958,576 A | 5/1976 | Komiya |
| 3,976,079 A | 8/1976 | Samuels et al. |
| 4,038,725 A | 8/1977 | Keefe |
| 4,103,690 A | 8/1978 | Harris |
| 4,140,125 A | 2/1979 | Smith ......................... 128/325 |

(List continued on next page.)

FOREIGN PATENT DOCUMENTS

| DE | 219999 | 5/1909 |
| DE | 21 99 99 | 3/1910 |
| DE | 27 03 529 A1 | 8/1978 |

(List continued on next page.)

OTHER PUBLICATIONS

International Search Report PCT/US99/12563.
"VCS Clip Applier Systems," published in 1995 by Auto Suture Company, a Division of U.S. Surgical Corporation, Norwalk, CT (8 pages).

(List continued on next page.)

Primary Examiner—Michael J. Milano
Assistant Examiner—(Jackie) Tan-Uyen T. Ho
(74) Attorney, Agent, or Firm—Harry J. Macey

(57) ABSTRACT

A tissue connector assembly comprising a clip movable between an open configuration and a closed configuration and a mechanical restraining device attached to the clip for restraining the clip in its open configuration. A needle may be releasably attached to the clip. A method for connecting tissues is also disclosed. The method includes inserting a clip through tissue with the clip being biased in an open position by a restraining device secured to the clip, and removing the restraining device from the clip.

48 Claims, 12 Drawing Sheets

U.S. PATENT DOCUMENTS

| | | | | |
|---|---|---|---|---|
| 4,170,990 | A | 10/1979 | Baumgart et al. | 128/92 |
| 4,192,315 | A | 3/1980 | Hilzinger et al. | 128/346 |
| 4,217,902 | A * | 8/1980 | March | 606/158 |
| 4,324,248 | A | 4/1982 | Perlin | 128/325 |
| 4,345,601 | A * | 8/1982 | Fukuda | 606/222 |
| 4,416,266 | A | 11/1983 | Baucom | 128/325 |
| 4,456,017 | A | 6/1984 | Miles | 128/772 |
| 4,485,816 | A | 12/1984 | Krumme | 128/334 |
| 4,522,207 | A | 6/1985 | Klieman et al. | 128/325 |
| 4,535,764 | A * | 8/1985 | Ebert | 606/222 |
| 4,549,545 | A | 10/1985 | Levy | |
| 4,586,502 | A | 5/1986 | Bedi et al. | |
| 4,586,503 | A | 5/1986 | Kirsch et al. | 128/334 |
| 4,595,007 | A | 6/1986 | Mericle | 128/334 |
| 4,612,932 | A | 9/1986 | Caspar et al. | 128/334 |
| 4,637,380 | A | 1/1987 | Orejola | 128/334 |
| 4,665,906 | A | 5/1987 | Jervis | 128/92 |
| 4,683,895 | A | 8/1987 | Pohndorf | 128/784 |
| 4,719,924 | A | 1/1988 | Crittenden et al. | 128/772 |
| 4,730,615 | A | 3/1988 | Sutherland et al. | |
| 4,809,695 | A | 3/1989 | Gwathmey et al. | 128/334 |
| 4,873,975 | A | 10/1989 | Walsh et al. | 128/334 |
| 4,896,668 | A | 1/1990 | Popoff et al. | |
| 4,899,744 | A | 2/1990 | Fujitsuka et al. | 606/153 |
| 4,901,721 | A | 2/1990 | Hakki | 606/103 |
| 4,924,866 | A | 5/1990 | Yoon | 128/335 |
| 4,926,860 | A | 5/1990 | Stice et al. | |
| 4,929,240 | A | 5/1990 | Kirsch et al. | 606/151 |
| 4,932,955 | A * | 6/1990 | Merz et al. | 606/158 |
| 4,950,283 | A | 8/1990 | Dzubow et al. | 606/216 |
| 4,950,285 | A | 8/1990 | Wilk | 606/232 |
| 4,983,176 | A | 1/1991 | Cushman et al. | 606/151 |
| 4,990,152 | A | 2/1991 | Yoon | |
| 4,997,439 | A | 3/1991 | Chen | 606/216 |
| 5,002,550 | A | 3/1991 | Li | 606/139 |
| 5,002,562 | A * | 3/1991 | Oberlander | 606/221 |
| 5,002,563 | A * | 3/1991 | Pyka et al. | 606/222 |
| 5,026,379 | A | 6/1991 | Yoon | |
| 5,047,047 | A | 9/1991 | Yoon | 606/216 |
| 5,053,047 | A | 10/1991 | Yoon | 606/223 |
| 5,074,874 | A | 12/1991 | Yoon et al. | 606/224 |
| 5,100,418 | A | 3/1992 | Yoon et al. | |
| 5,123,913 | A | 6/1992 | Wilk et al. | 606/232 |
| 5,152,769 | A | 10/1992 | Baber | 606/145 |
| 5,154,189 | A | 10/1992 | Oberlander | 128/898 |
| 5,158,566 | A | 10/1992 | Pianetti | 606/216 |
| 5,171,250 | A | 12/1992 | Yoon | |
| 5,171,252 | A | 12/1992 | Friedland | 606/151 |
| 5,174,087 | A | 12/1992 | Bruno | |
| 5,196,022 | A | 3/1993 | Bilweis | |
| 5,219,358 | A | 6/1993 | Bendel et al. | 606/222 |
| 5,222,976 | A | 6/1993 | Yoon | 606/223 |
| 5,236,440 | A | 8/1993 | Hlavacek | 606/219 |
| 5,242,456 | A | 9/1993 | Nash et al. | |
| 5,246,443 | A | 9/1993 | Mai | 606/78 |
| 5,258,011 | A | 11/1993 | Drews | 606/220 |
| 5,269,783 | A | 12/1993 | Sander | |
| 5,290,289 | A | 3/1994 | Sanders et al. | 606/61 |
| 5,304,204 | A | 4/1994 | Bregen | |
| 5,312,436 | A | 5/1994 | Coffey et al. | 606/228 |
| 5,330,503 | A | 7/1994 | Yoon | 606/223 |
| 5,336,239 | A | 8/1994 | Gimpleson | 606/223 |
| 5,356,424 | A | 10/1994 | Buzerak et al. | |
| 5,374,268 | A | 12/1994 | Sander | |
| 5,383,904 | A | 1/1995 | Totakura et al. | |
| 5,403,346 | A | 4/1995 | Loeser | |
| 5,437,680 | A | 8/1995 | Yoon | 606/139 |
| 5,437,685 | A | 8/1995 | Blasnik | |
| 5,439,479 | A | 8/1995 | Shichman et al. | 606/220 |
| 5,445,167 | A | 8/1995 | Yoon et al. | 128/898 |
| 5,452,733 | A | 9/1995 | Sterman et al. | |
| 5,456,246 | A | 10/1995 | Schmieding et al. | |
| 5,462,561 | A | 10/1995 | Voda | |
| 5,474,557 | A | 12/1995 | Mai | 606/78 |
| 5,480,405 | A | 1/1996 | Yoon | 606/139 |
| 5,486,197 | A | 1/1996 | Le et al. | |
| 5,499,990 | A | 3/1996 | Schulken et al. | |
| 5,500,000 | A | 3/1996 | Feagin et al. | 606/232 |
| 5,527,342 | A | 6/1996 | Pietrzak et al. | |
| 5,549,619 | A | 8/1996 | Peters et al. | 606/151 |
| 5,569,274 | A | 10/1996 | Rapacki et al. | |
| 5,569,301 | A | 10/1996 | Granger et al. | 606/224 |
| 5,582,616 | A | 12/1996 | Bolduc et al. | 606/143 |
| 5,582,619 | A | 12/1996 | Ken | |
| 5,586,983 | A | 12/1996 | Sanders et al. | 606/61 |
| 5,591,179 | A | 1/1997 | Edelstein | 606/144 |
| 5,593,414 | A | 1/1997 | Shipp et al. | 606/142 |
| 5,593,424 | A | 1/1997 | Northrup, III | |
| 5,609,608 | A | 3/1997 | Benett et al. | |
| 5,632,752 | A | 5/1997 | Buelna | 606/114 |
| 5,632,753 | A | 5/1997 | Loeser | 606/151 |
| 5,643,295 | A | 7/1997 | Yoon | 606/151 |
| 5,645,568 | A | 7/1997 | Chervitz et al. | |
| 5,665,109 | A | 9/1997 | Yoon | 606/232 |
| 5,683,417 | A | 11/1997 | Cooper | 606/223 |
| 5,695,505 | A | 12/1997 | Yoon | |
| 5,697,943 | A | 12/1997 | Sauer et al. | 606/153 |
| 5,700,270 | A | 12/1997 | Peyser et al. | 606/142 |
| 5,700,271 | A | 12/1997 | Whitfield et al. | 606/143 |
| 5,707,380 | A | 1/1998 | Hinchliffe et al. | 606/153 |
| 5,709,693 | A | 1/1998 | Taylor | 606/145 |
| 5,709,695 | A | 1/1998 | Northup, III | |
| 5,725,539 | A | 3/1998 | Matern | 606/151 |
| 5,725,542 | A | 3/1998 | Yoon | |
| 5,728,135 | A | 3/1998 | Bregen et al. | |
| 5,735,290 | A | 4/1998 | Sterman et al. | |
| 5,799,661 | A | 9/1998 | Boyd et al. | |
| 5,810,851 | A * | 9/1998 | Yoon | 606/148 |
| 5,810,882 | A | 9/1998 | Bolduc et al. | |
| 5,820,631 | A | 10/1998 | Nobles | |
| 5,824,008 | A | 10/1998 | Bolduc et al. | |
| 5,830,221 | A | 11/1998 | Stein et al. | |
| 5,849,019 | A | 12/1998 | Yoon | |
| 5,879,371 | A | 3/1999 | Gardiner et al. | |
| 5,891,130 | A | 4/1999 | Palermo et al. | |
| 5,891,160 | A | 4/1999 | Williamson, IV et al. | |
| 5,895,394 | A | 4/1999 | Kienzle et al. | |
| 5,961,481 | A | 10/1999 | Sterman et al. | |
| 5,961,539 | A | 10/1999 | Northrup, III et al. | |
| 5,964,772 | A | 10/1999 | Bolduc et al. | |
| 5,972,024 | A | 10/1999 | Northrup, III et al. | |
| 5,976,159 | A | 11/1999 | Bolduc et al. | |
| 5,984,917 | A | 11/1999 | Fleischman et al. | |
| 5,989,242 | A | 11/1999 | Saadat et al. | |
| 5,989,268 | A | 11/1999 | Pugsley, Jr. et al. | |
| 5,997,556 | A | 12/1999 | Tanner | |
| 6,001,110 | A | 12/1999 | Adams | |
| 6,013,084 | A | 1/2000 | Ken et al. | |
| 6,074,401 | A | 6/2000 | Gardiner et al. | |
| 6,132,438 | A | 10/2000 | Fleischman et al. | |
| 6,139,540 | A | 10/2000 | Rost et al. | |
| 6,143,004 | A | 11/2000 | Davis et al. | |
| 6,149,658 | A | 11/2000 | Gardiner et al. | |
| 6,176,413 | B1 | 1/2001 | Heck et al. | |
| 6,190,373 | B1 | 2/2001 | Palermo et al. | |
| 6,193,733 | B1 | 2/2001 | Adams | |
| 6,193,734 | B1 | 2/2001 | Bolduc et al. | |
| 6,254,615 | B1 | 7/2001 | Bolduc et al. | |
| 6,296,656 | B1 | 10/2001 | Bolduc et al. | |
| 6,346,112 | B2 | 2/2002 | Adams | |

FOREIGN PATENT DOCUMENTS

| | | |
|---|---|---|
| DE | 32 03 410 A1 | 11/1982 |
| DE | 32 27 984 A1 | 2/1984 |
| DE | 41 33 800 C1 | 1/1993 |
| DE | 44 02 058 C1 | 4/1995 |
| DE | 195 47 617 C1 | 9/1997 |
| EP | 0 121 362 B1 | 10/1984 |
| EP | 0140557 A2 | 5/1985 |
| EP | 0 326 426 B1 | 8/1989 |
| EP | 0 432 692 A1 | 6/1991 |
| EP | 0 478 949 B1 | 4/1992 |
| EP | 0 494 636 A1 | 7/1992 |
| EP | 0 537 955 B1 | 4/1993 |
| EP | 0 559 429 A1 | 9/1993 |
| EP | 0 419 597 B1 | 12/1994 |
| EP | 0 641 546 A1 | 3/1995 |
| EP | 0 711 532 A1 | 5/1996 |
| EP | 0 734 697 A2 | 10/1996 |
| EP | 0 778 005 A1 | 6/1997 |
| EP | 0 815 795 A1 | 1/1998 |
| GB | 2 223 410 | 4/1990 |
| JP | 10337291 A | 12/1998 |
| RU | 2110222 C1 | 5/1998 |
| SU | 1186199 A | 10/1985 |
| SU | 1456109 A1 | 2/1989 |
| SU | 1560133 A1 | 4/1990 |
| WO | WO 90/06725 A1 | 6/1990 |
| WO | WO 90/09149 A1 | 8/1990 |
| WO | WO 90/14795 A1 | 12/1990 |
| WO | WO 91/07916 A1 | 6/1991 |
| WO | WO 91/17712 | 11/1991 |
| WO | WO 92/05828 A1 | 4/1992 |
| WO | WO 94/15535 A1 | 7/1994 |
| WO | WO 94/15537 | 7/1994 |
| WO | WO 96/00035 | 1/1996 |
| WO | WO 96/06565 A1 | 3/1996 |
| WO | WO 96/38090 A1 | 12/1996 |
| WO | WO 97/28744 A1 | 8/1997 |
| WO | WO 97/32526 A1 | 9/1997 |
| WO | WO 97/42881 | 11/1997 |
| WO | WO 98/30153 A1 | 7/1998 |
| WO | WO 98/42262 | 10/1998 |

OTHER PUBLICATIONS

"VSC Clip Applier System" (advertizing brochure) USSC © 1995.

Emery, R.W. et al. (1997. "Suture techniques for MIDCAB Surgery" Chapter 12 in *Techniques for Minimally Invasive Direct Coronary Artery Bypass (MIDCAB) Surgery*. R.W. Emery ed. Philadelphia: Hanley &Belfus, Inc., pp. 87–91.

Wylie, E. J. et al., (1980). *Manual of Vascular Surgery*. R.H. Egdahl ed., New York: Springer–Verlag, vol. 1 and 2, 10 pages. Title pages and table of contents only.

Written Opinion, PCT/US99/12563, Jun. 12, 2000.

* cited by examiner

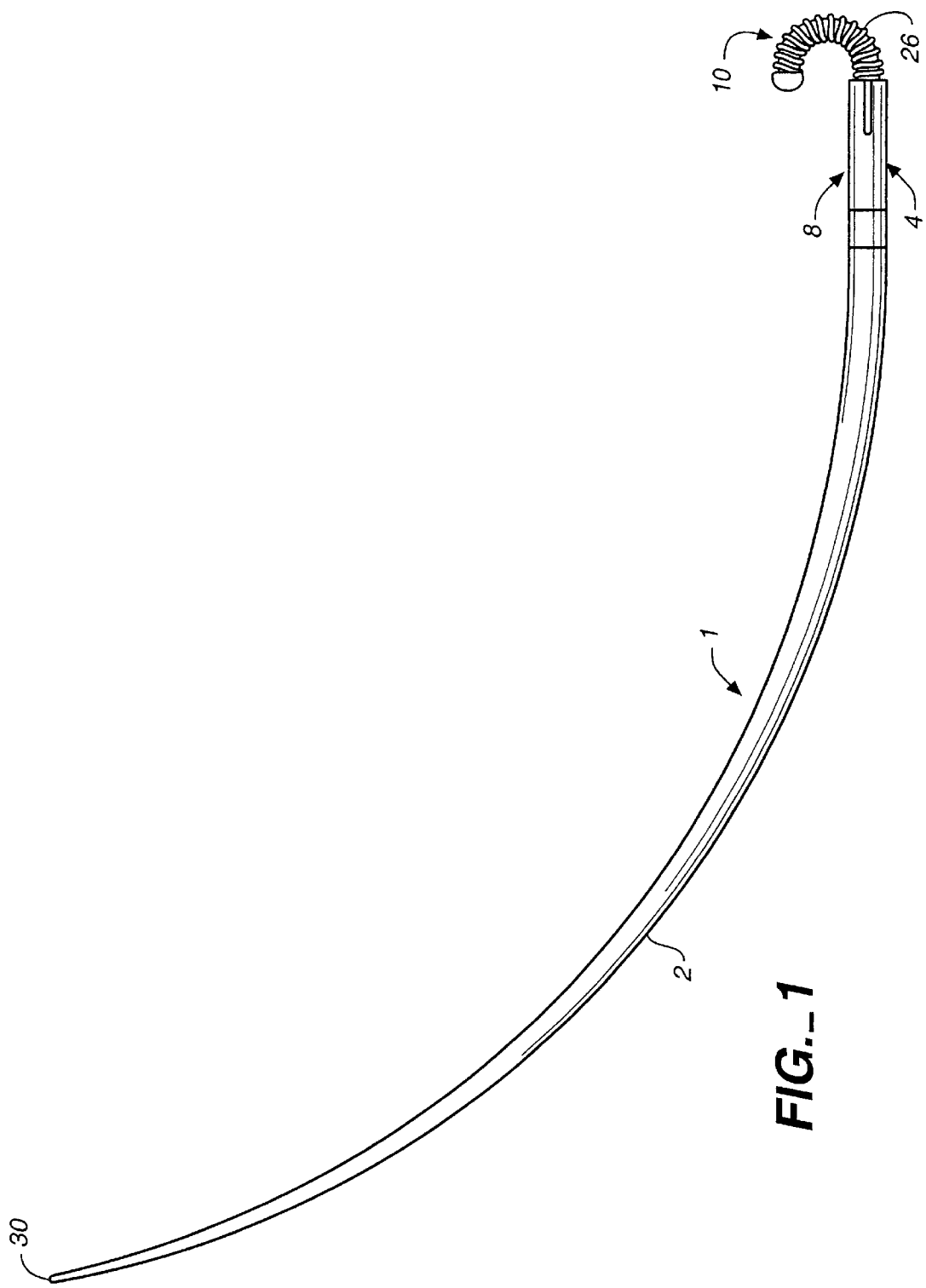
FIG._1

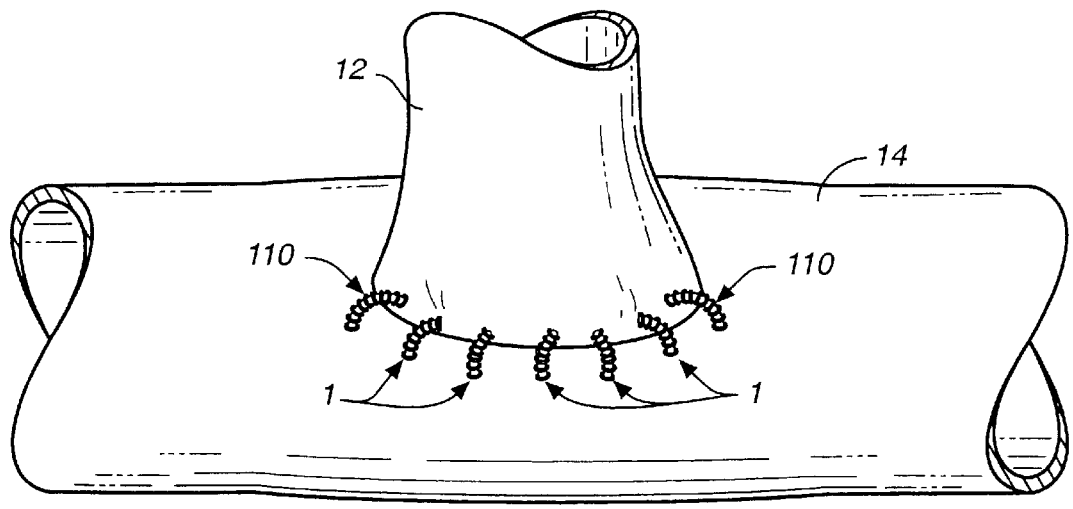
FIG._2A
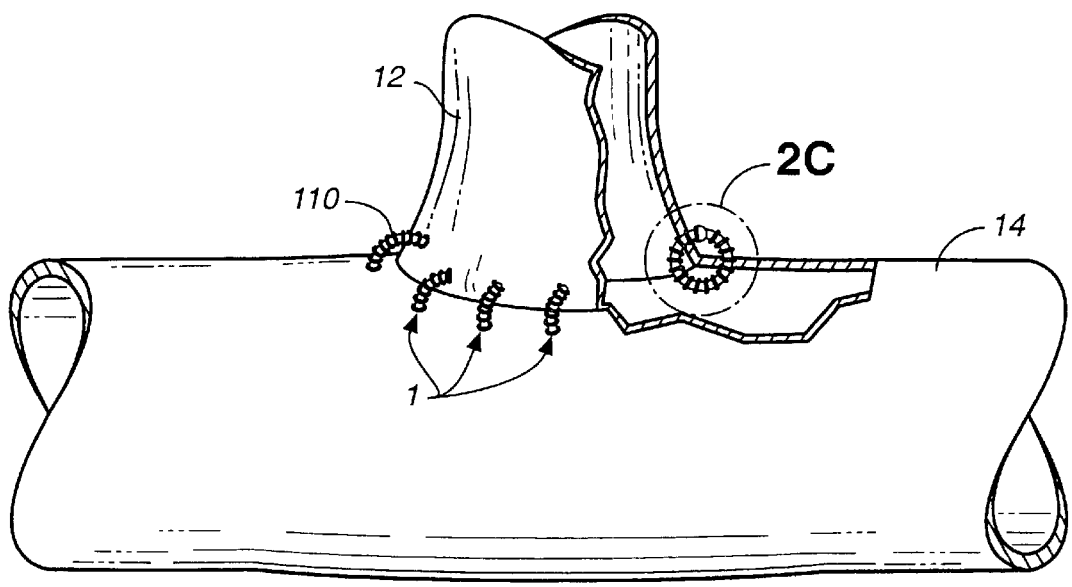
FIG._2B

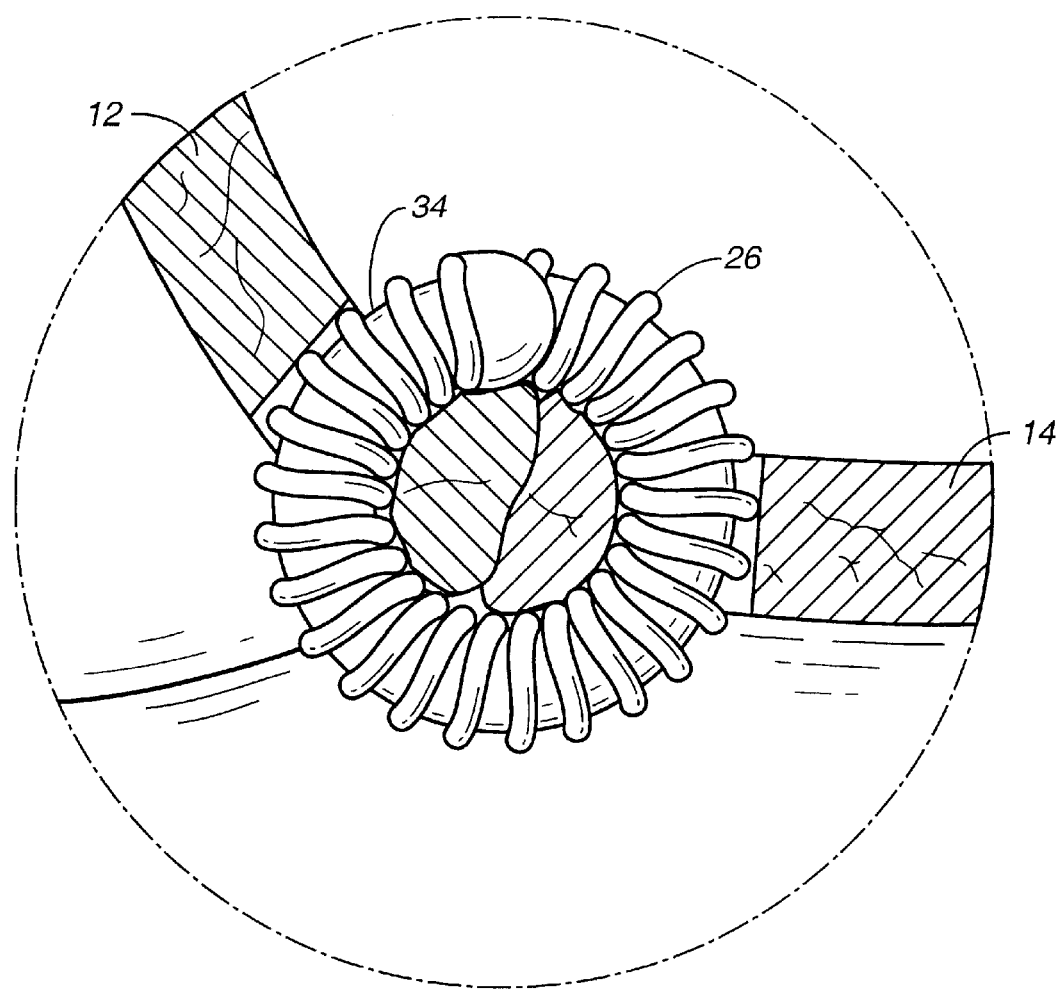
FIG._2C

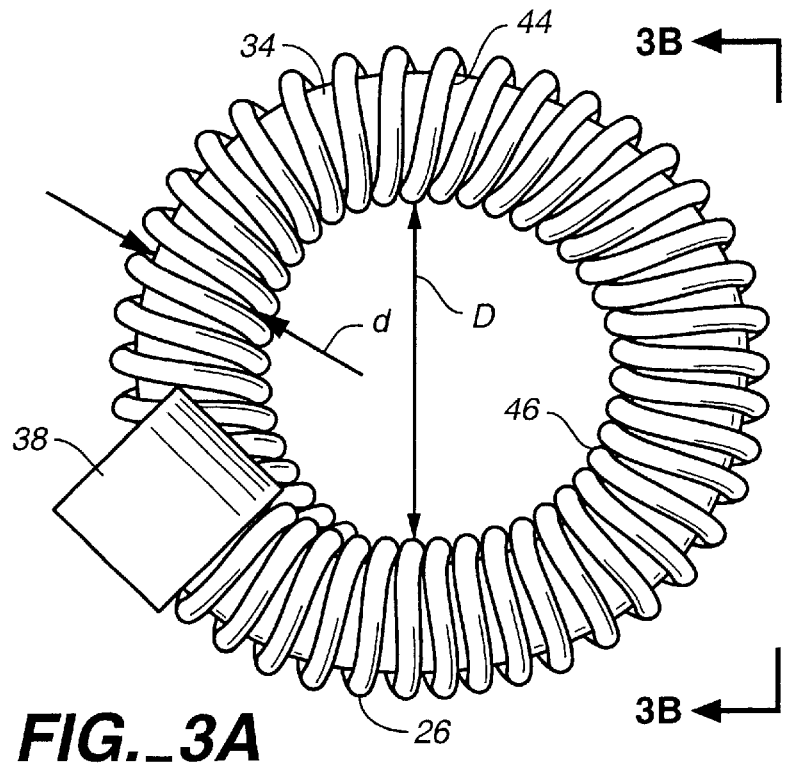
FIG._3A
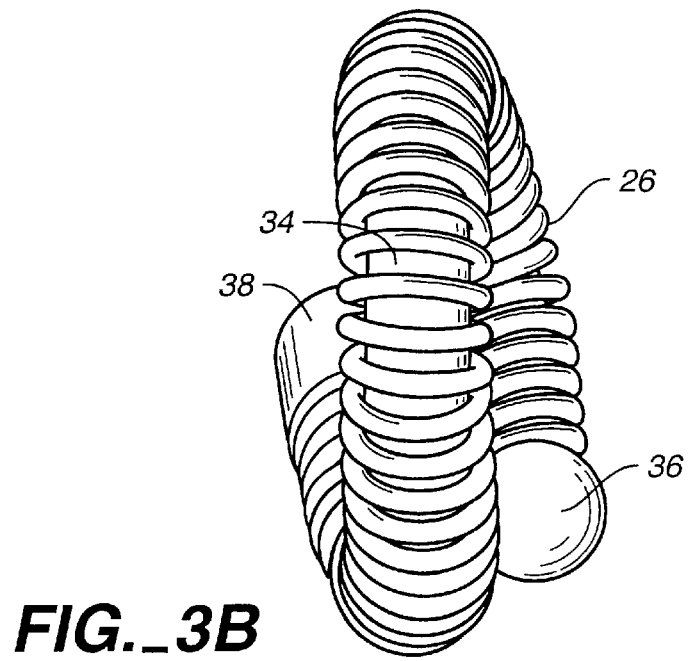
FIG._3B

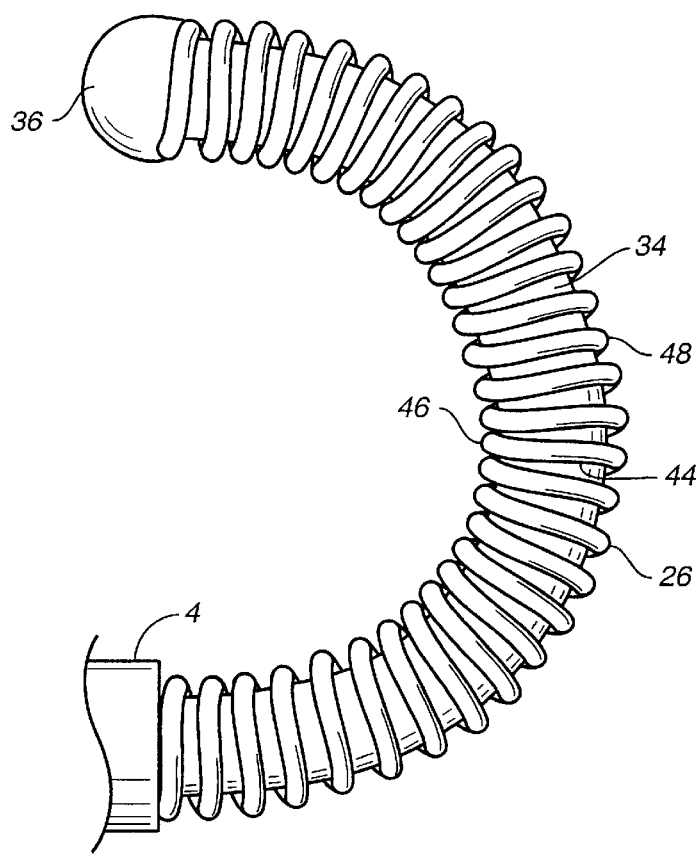
FIG._3C
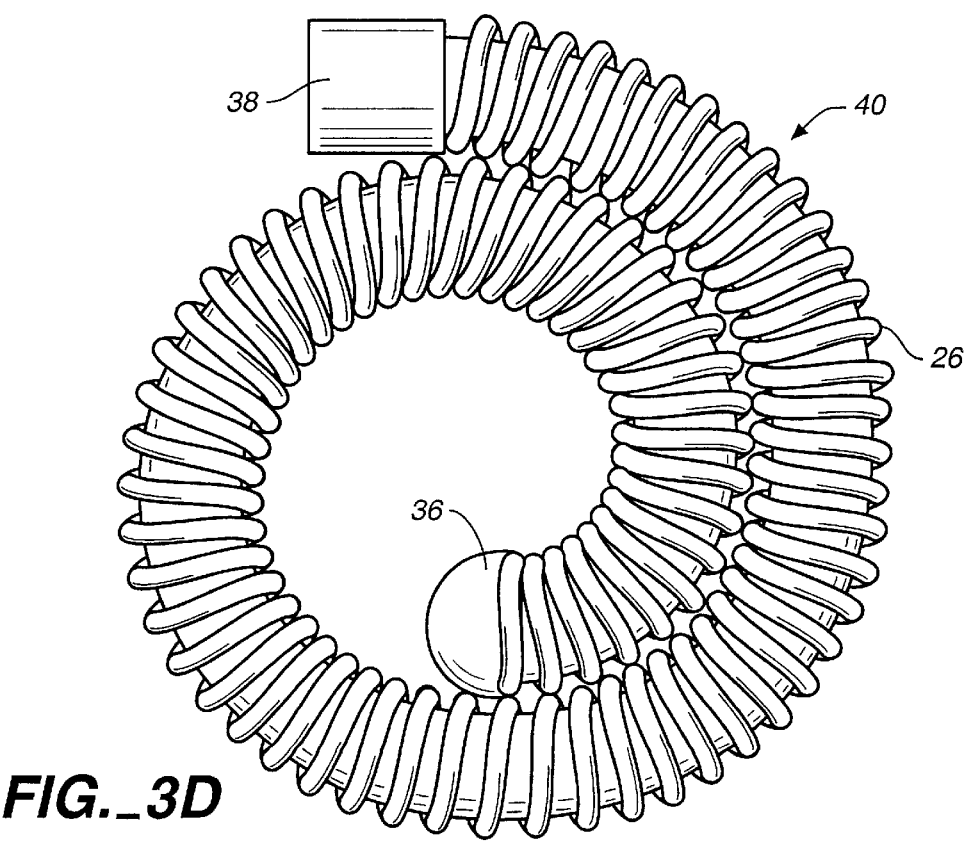
FIG._3D

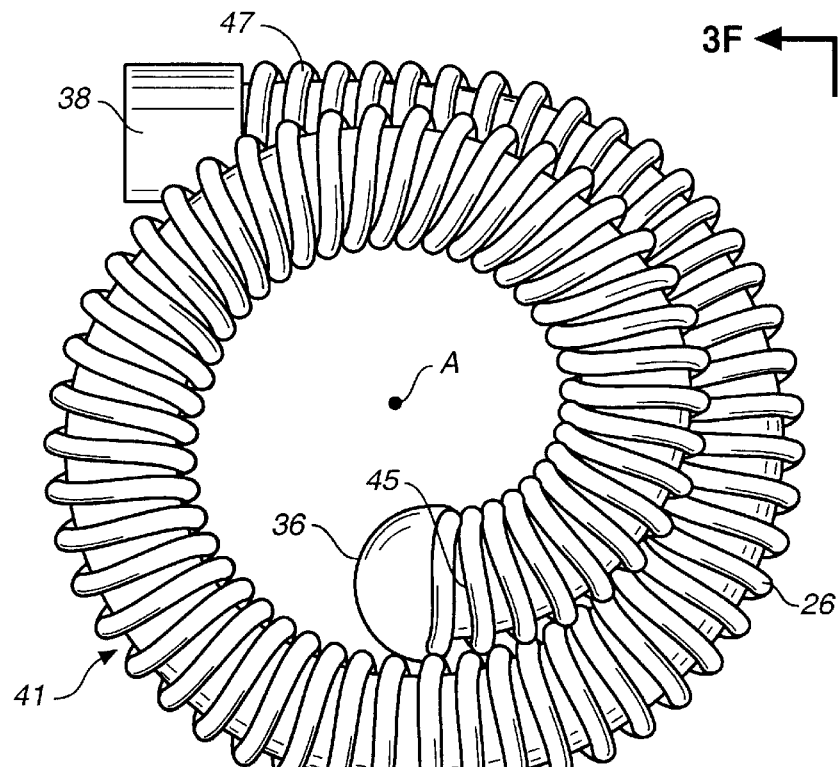
FIG._3E
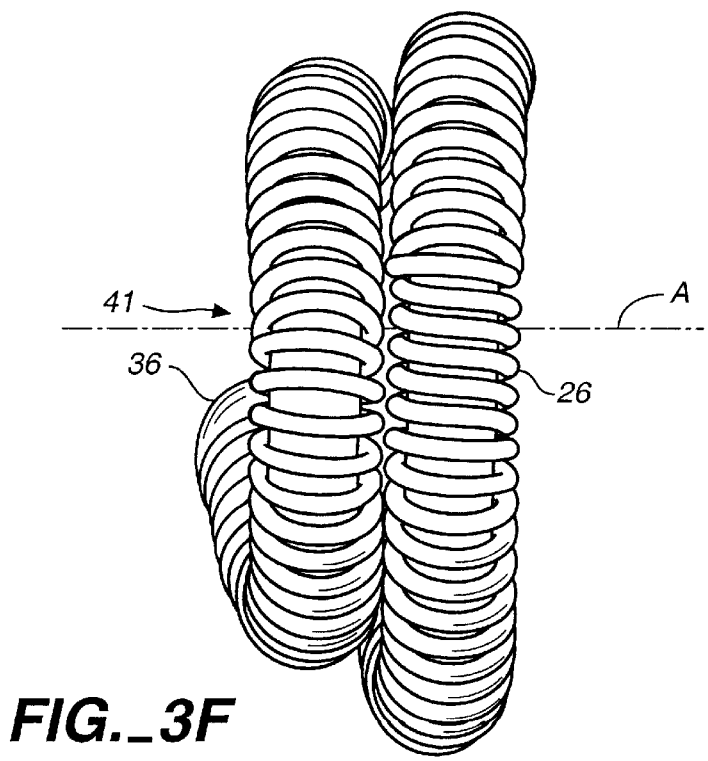
FIG._3F

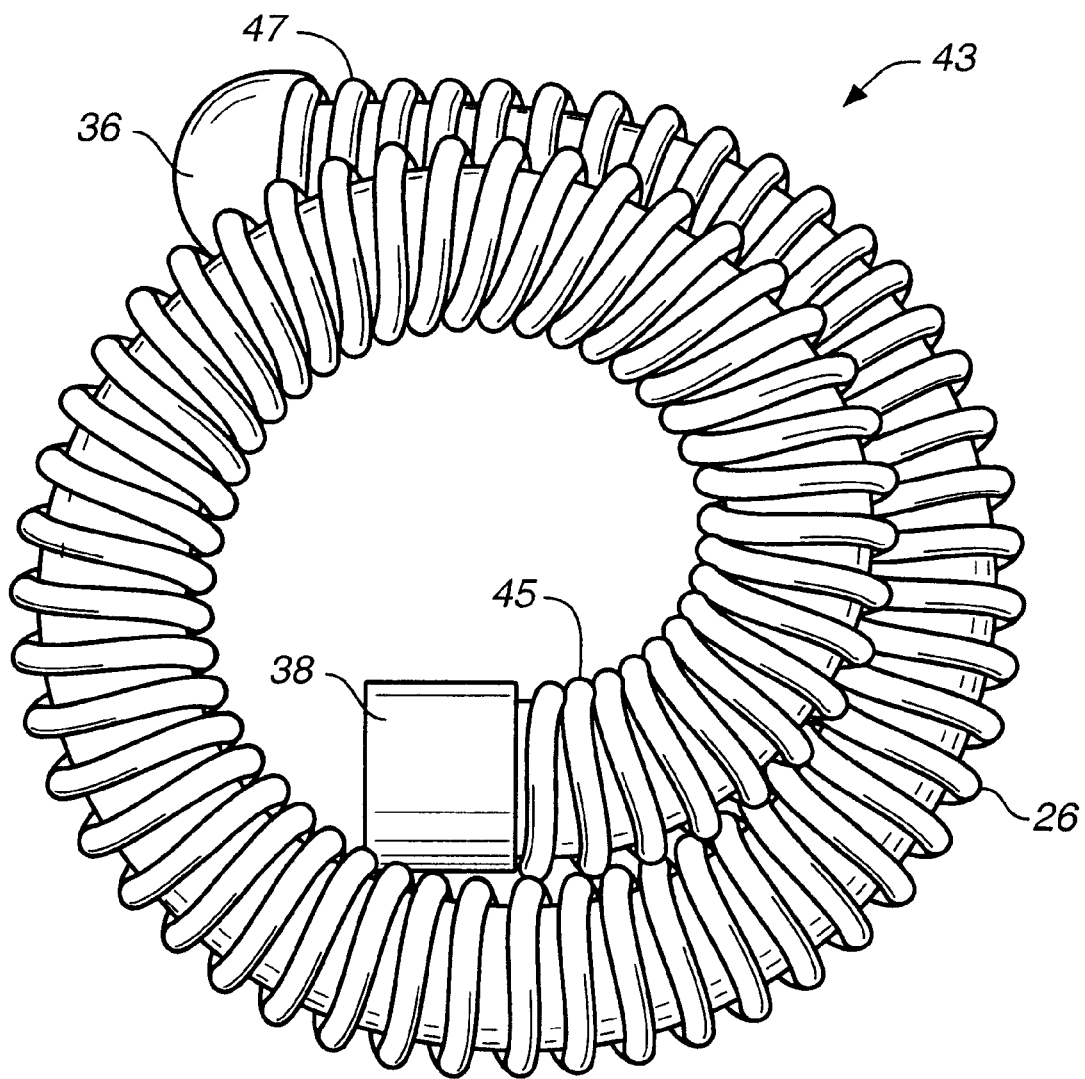
FIG._3G

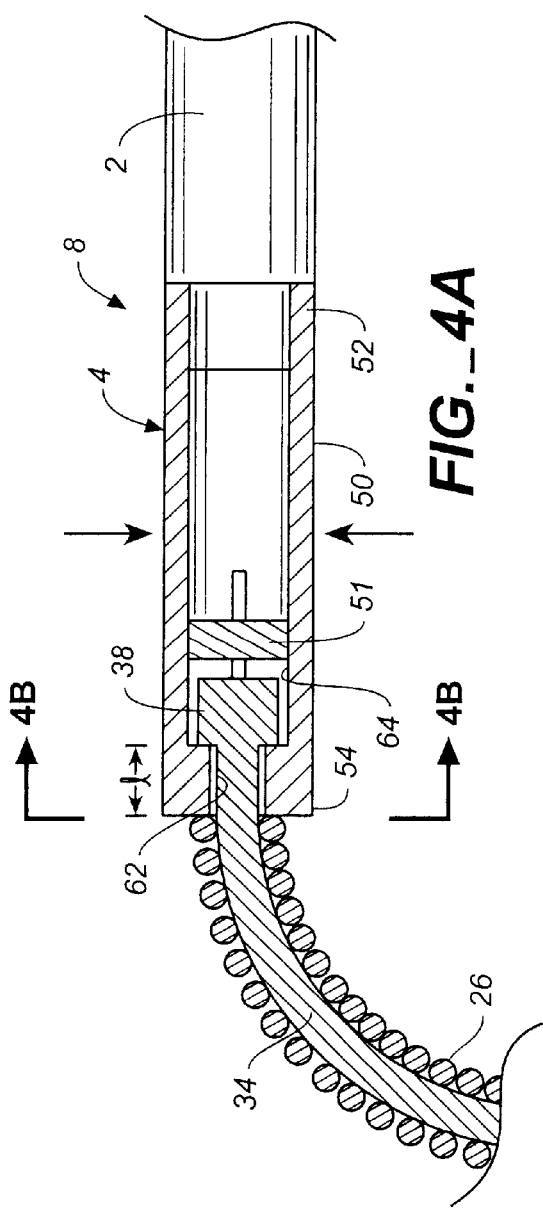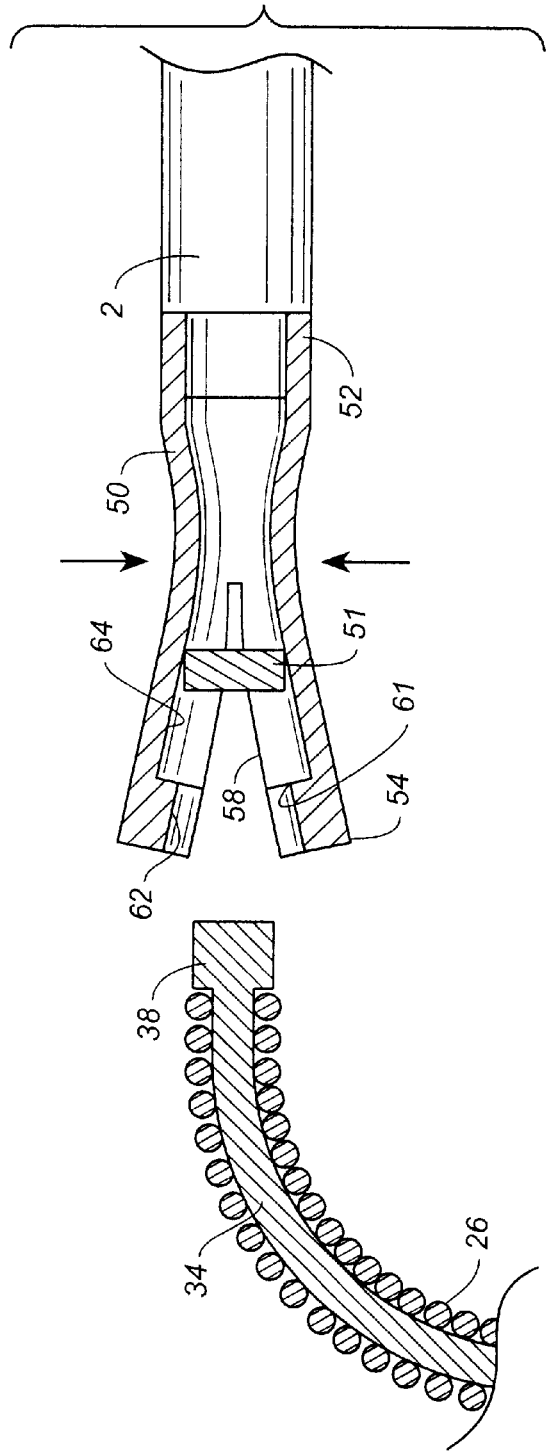

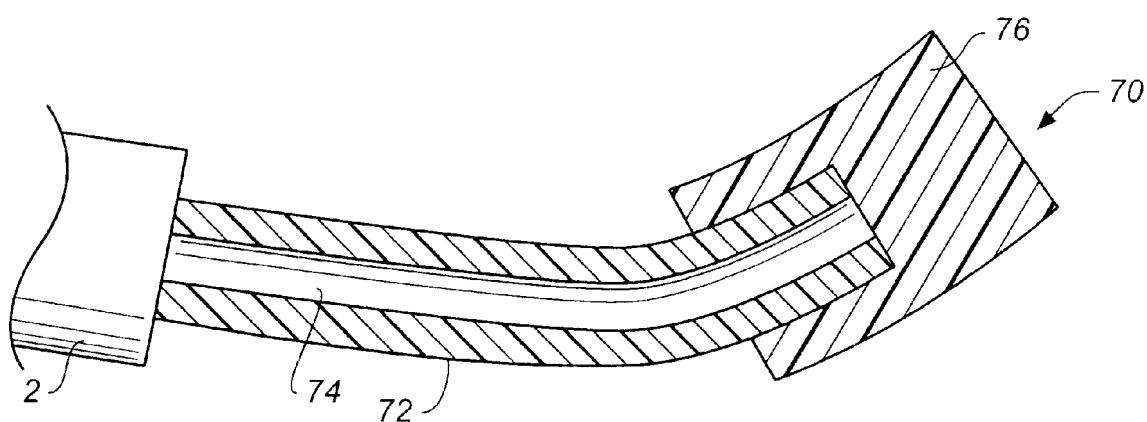
FIG._5

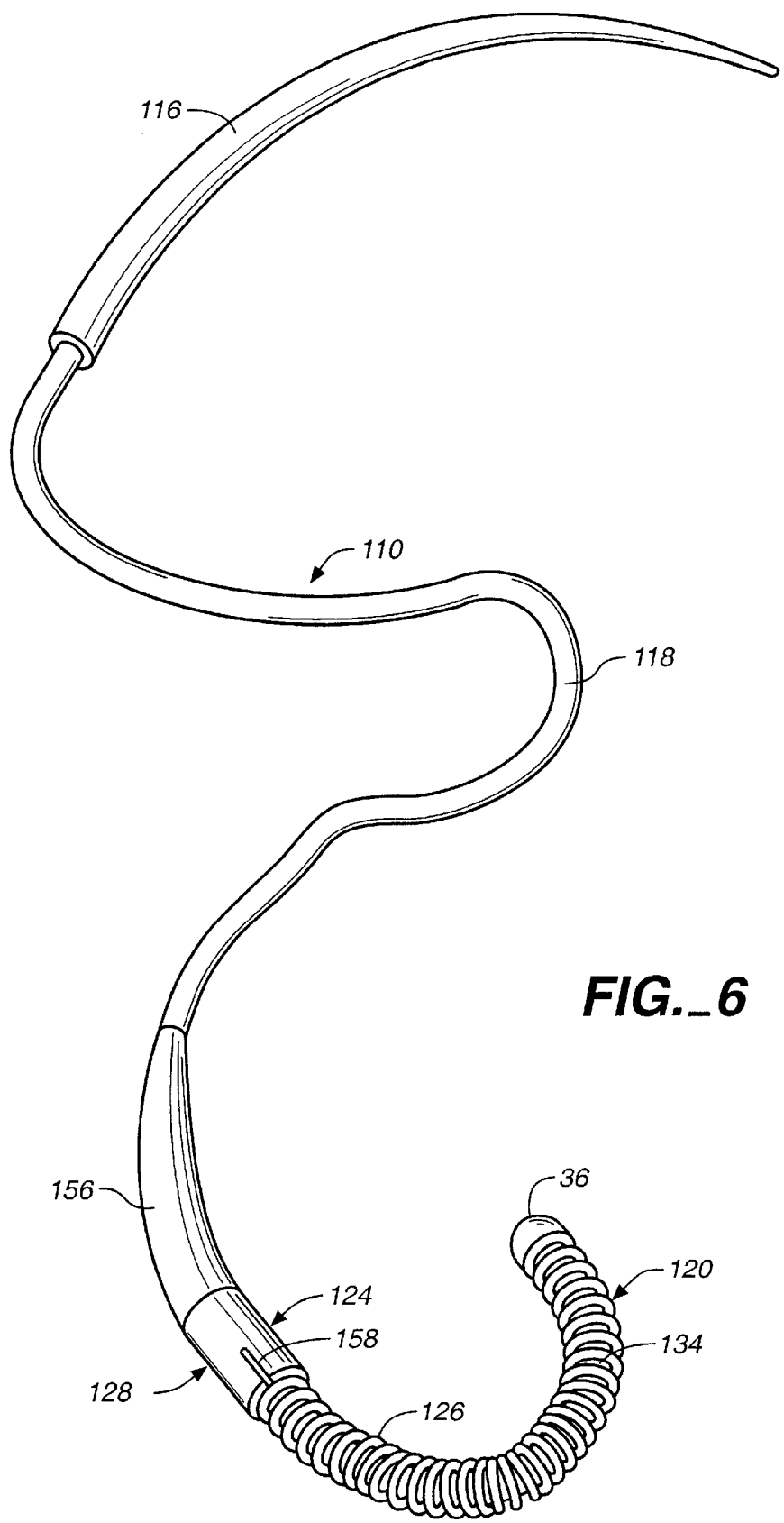
FIG._6

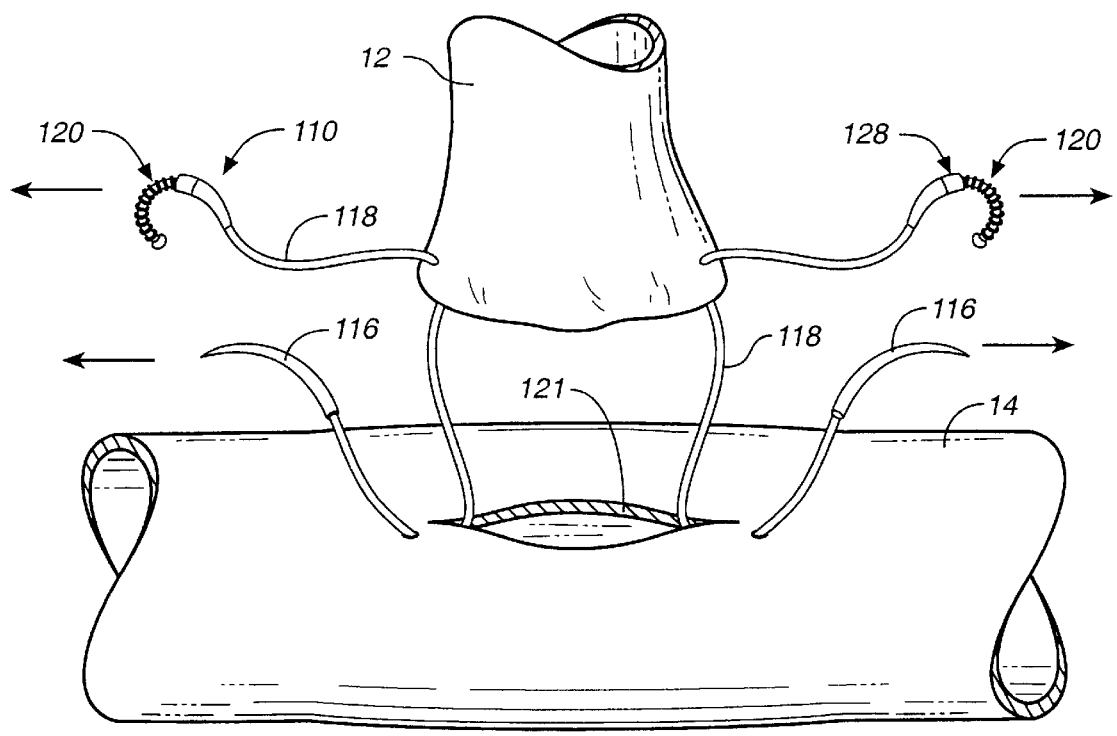
*FIG._7*
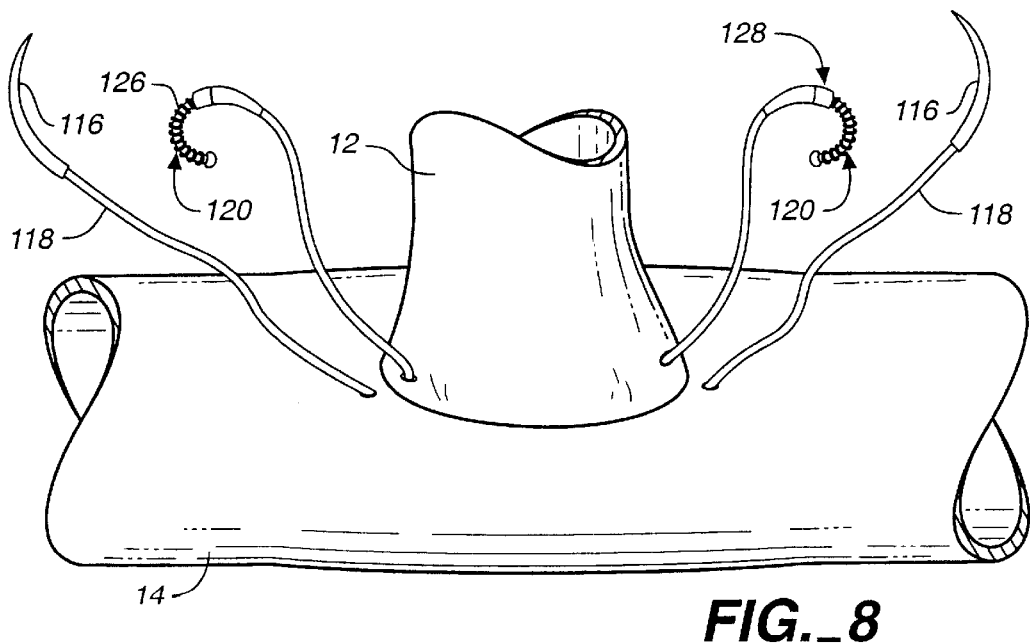
*FIG._8*

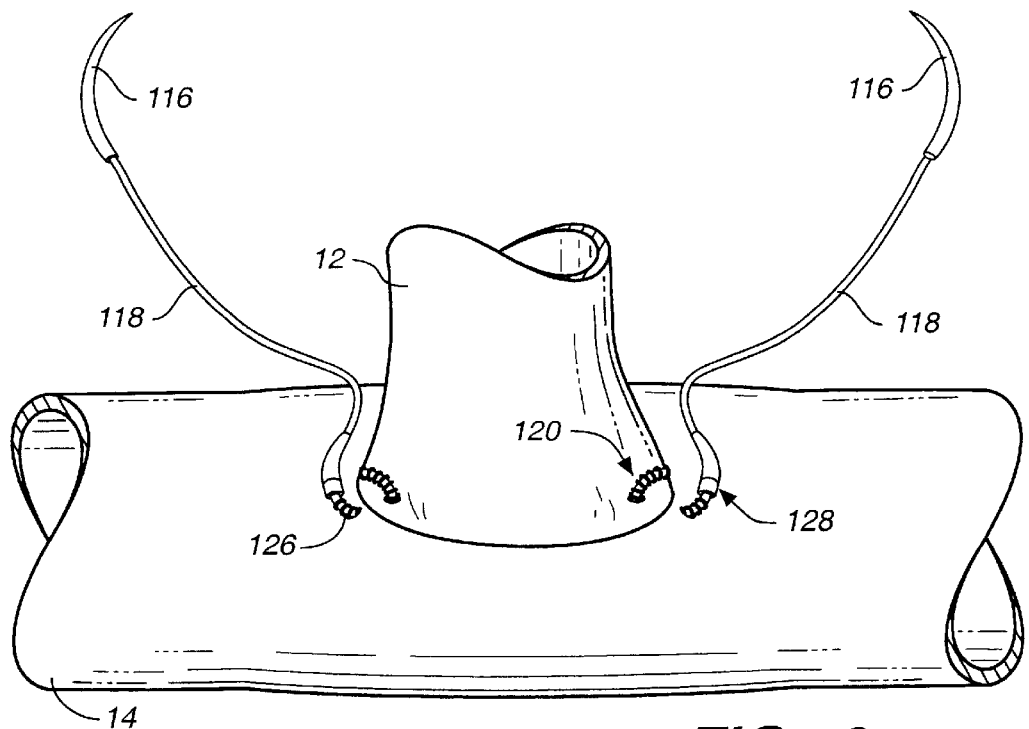
FIG._9
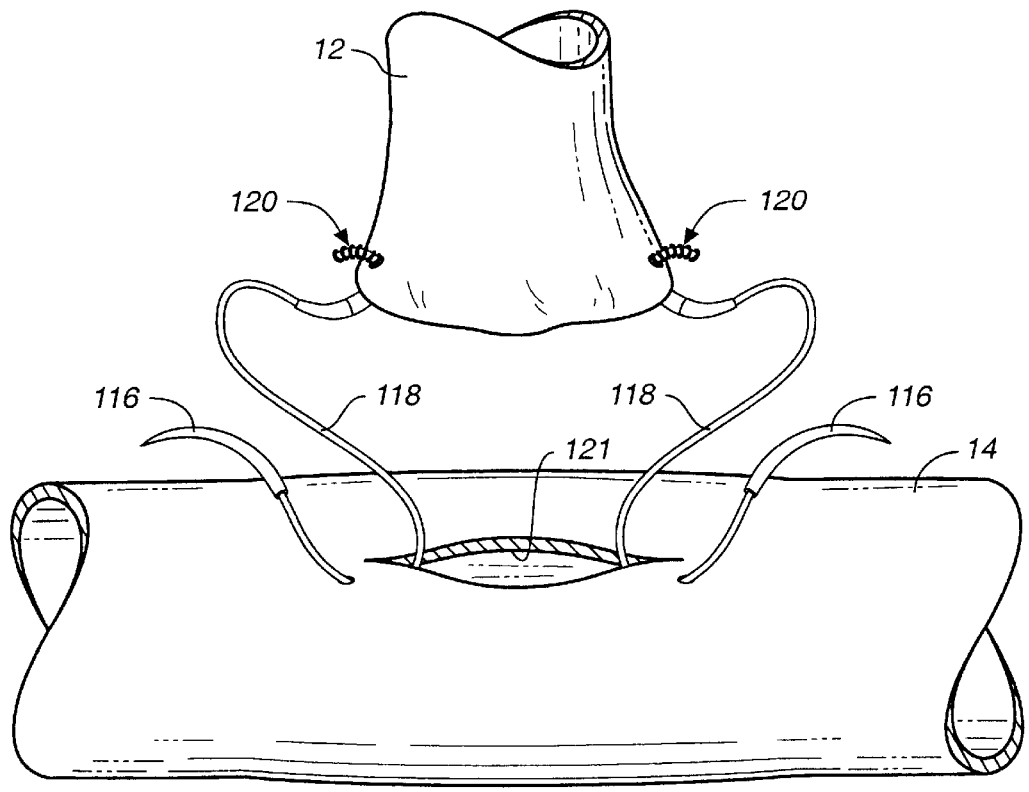
FIG._10

TISSUE CONNECTOR APPARATUS AND METHODS

FIELD OF THE INVENTION

The present invention relates to instruments and methods for connecting body tissues, or body tissue to prostheses.

BACKGROUND OF THE INVENTION

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trocar, which is a pointed, piercing device, is delivered into the body with a cannula. After the trocar pierces the abdominal or thoracic wall, it is removed and the cannula is left with one end in the body cavity, where the operation is to take place, and the other end opening to the outside. A cannula has a small inside diameter, typically 5–10 millimeters, and sometimes up to as much as 20 millimeters. A number of such cannulas are inserted for any given operation.

A viewing instrument, typically including a miniature video camera, or optical telescope is inserted through one of these cannulas and a variety of surgical instruments and refractors are inserted through others. The image provided by the viewing device may be displayed on a video screen or television monitor, affording the surgeon enhanced visual control over the instruments. Because a commonly used viewing instrument is called an "endoscope," this type of surgery is often referred to as "endoscopic surgery." In the abdomen, endoscopic procedures are commonly referred to as laparoscopic surgery, and in the chest, as thoracoscopic surgery. Abdominal procedures may take place either inside the abdominal cavity (in the intraperitoneal space) or in a space created behind the abdominal cavity (in the retroperitoneal space). The retroperitoneal space is particularly useful for operations on the aorta and spine or abdominal wall hernia.

Minimally invasive surgery has virtually replaced open surgical techniques for operations such as cholecystectomy and anti-reflux surgery of the esophagus and stomach. This has not occurred in either peripheral vascular surgery or cardiovascular surgery. An important type of vascular surgery is to replace or bypass a diseased, occluded or injured artery. Arterial replacement or bypass grafting has been performed for many years using open surgical techniques and a variety of prosthetic grafts. These grafts are manufactured as fabrics (often from DACRON® (polyester fibers) or TEFLON® (fluorocarbon fibers)) or are prepared as autografts (from the patient's own tissues) or heterografts (from the tissues of animals) or a combination of tissues, semi-synthetic tissues and or alloplastic materials. A graft can be joined to the involved artery in a number of different positions, including end-to-end, end-to-side, and side-to-side. This attachment between artery and graft is known as an anastomosis. Constructing an arterial anastomosis is technically challenging for a surgeon in open surgical procedures, and is almost a technical impossibility using minimally invasive techniques.

Many factors contribute to the difficulty of performing arterial replacement or bypass grafting. See generally, Wylie, Edwin J. et al., Manual of Vascular Surgery, (Springer-Verlag New York), 1980. One such factor is that the tissues to be joined must be precisely aligned with respect to each other to ensure the integrity and patency of the anastomosis. If one of the tissues is affixed too close to its edge, the suture can rip through the tissue and impair both the tissue and the anastomosis. Another factor is that, even after the tissues are properly aligned, it is difficult and time consuming to pass the needle through the tissues, form the knot in the suture material, and ensure that the suture material does not become tangled. These difficulties are exacerbated by the small size of the artery and graft. The arteries subject to peripheral vascular and cardiovascular surgery typically range in diameter from several millimeters to several centimeters. A graft is typically about the same size as the artery to which it is being attached. Another factor contributing to the difficulty of such procedures is the limited time available to complete the procedure. The time the surgeon has to complete an arterial replacement or bypass graft is limited because there is no blood flowing through the artery while the procedure is being done. If blood flow is not promptly restored, sometimes in as little as thirty minutes, the tissue the artery supplies may experience significant damage, or even death (tissue necrosis). In addition, arterial replacement or bypass grafting is made more difficult by the need to accurately place and space many sutures to achieve a permanent hemostatic seal. Precise placement and spacing of sutures is also required to achieve an anastomosis with long-term patency.

Highly trained and experienced surgeons are able to perform arterial replacement and bypass grafting in open surgery using conventional sutures and suturing techniques. A suture has a suture needle that is attached or "swedged on" to a long, trailing suture material. The needle must be precisely controlled and accurately placed through both graft and artery. The trailing suture material must be held with proper tension to keep the graft and artery together, and must be carefully manipulated to prevent the suture material from tangling. In open surgery, these maneuvers can usually be accomplished within the necessary time frame, thus avoiding the subsequent tissue damage (or tissue death) that can result from prolonged occlusion of arterial blood flow.

The difficulty of suturing a graft to an artery using minimally invasive surgical techniques has effectively prevented the safe use of this technology in both peripheral vascular and cardiovascular surgical procedures. When a minimally invasive procedure is done in the abdominal cavity, the retroperitoneal space, or chest, the space in which the operation is performed is more limited, and the exposure to the involved organs is more restricted, than with open surgery. Moreover, in a minimally invasive procedure, the instruments used to assist with the operation are passed into the surgical field through cannulas. When manipulating instruments through cannulas, it is extremely difficult to position tissues in their proper alignment with respect to each other, pass a needle through the tissues, form a knot in the suture material once the tissues are aligned, and prevent the suture material from becoming tangled. Therefore, although there have been isolated reports of vascular anastomoses being formed by minimally invasive surgery, no system has been provided for wide-spread surgical use which would allow such procedures to be performed safely within the prescribed time limits.

As explained above, anastomoses are commonly formed in open surgery by suturing together the tissues to be joined. However, one known system for applying a clip around tissues to be joined in an anastomosis is disclosed in a brochure entitled, "VCS Clip Applier System", published in 1995 by Auto Suture Company, a Division of U.S. Surgical Corporation. A clip is applied by applying an instrument about the tissue in a nonpenetrating manner, i.e., the clip does not penetrate through the tissues, but rather is clamped down around the tissues. As previously explained, it is imperative in forming an anastomosis that tissues to be joined are properly aligned with respect to each other. The disclosed VCS clip applier has no means for positioning tissues. Before the clip can be applied, the tissues must first be properly positioned with respect to each other, for example by skewering the tissues with a needle as discussed above in common suturing techniques or with forceps to bring the tissues together. It is extremely difficult to perform such positioning techniques in minimally invasive procedures.

Therefore, there is currently a need for other tissue connector assemblies.

SUMMARY OF THE INVENTION

The present invention involves improvements to devices and methods for connecting tissues or tissue(s) and grafts, such as in a vascular anastomosis. The invention generally involves a surgical clip which is self-closing. Preferably, the surgical clip comprises a shape memory material, most preferably nitinol.

According to one aspect of the invention, a tissue connector assembly is provided with a clip movable between an open configuration and a closed configuration, and a mechanical restraining device attached to the clip for restraining the clip in its open configuration. The clip may have a generally U-shaped configuration when in its open configuration.

The mechanical restraining device may include a coil for biasing the clip in its open configuration. Alternatively, the clip may include a tubular wire and the mechanical restraining device may include an elongated member that is positionable within the tubular wire.

According to another aspect of the present invention, a tissue connector assembly generally comprises a clip having a spiral shaped configuration when in a closed configuration and an open configuration wherein the clip is configured to form less than a full 360 degree turn. The spiral may be formed in one plane or may extend from a plane of a first loop of the spiral to form a generally conical shaped helical clip. The spiral shaped configuration of the clip generally provides for tight compression of the connecting tissue and may reduce the amount of surface area of the clip exposed to blood flow in an anastomosis, for example.

A needle may be attached to the clip for piercing tissue/graft material, and may be releasably attached to facilitate removal of the needle after insertion of the clip. The clip is generally small enough to prevent obstruction of a surgeon's view of the tissue being connected and allow for precise control of the clip by the surgeon.

In another aspect of the invention, a locking device is provided for releasably locking the clip in its open configuration. Upon release of the locking device a restraining force is removed from the clip to allow the clip to move to its unbiased, closed position. Advantageously, the locking device may also be arranged to removably connect a needle to the clip. Upon release of the locking device, the needle is disconnected from the clip. Both removal of the needle and release of the biasing force from the clip may occur simultaneously.

A method of the present invention generally includes inserting a clip through tissue with the clip biased in an open position by a restraining device coupled to the clip, and removing the restraining force on the clip to allow the clip to close.

Another aspect of the present invention generally includes inserting a needle and a clip attached to the needle through tissue with an instrument, with the ability to remove the needle from the clip with the same instrument. The present invention may allow a surgeon to single handedly insert and close the clip to connect tissue using a minimum amount of instruments.

The above is a brief description of some deficiencies in the prior art and advantages of the present invention. Other features, advantages, and embodiments of the invention will be apparent to those skilled in the art from the following description, accompanying drawings, and claims.

BRIEF DESCRIPTION OF THE DRAWINGS

FIG. 1 is a front view of a tissue connector assembly of the present invention;

FIG. 2A shows a graft vessel connected to a target vessel with tissue connector assemblies of FIG. 1;

FIG. 2B is a front view of the connected graft and target vessels of FIG. 2A, with portions broken away to show detail;

FIG. 2C is an enlarged view of the tissue connection shown in FIG. 2B;

FIG. 3A is an enlarged view of a fastener of the tissue connector assembly of FIG. 1 shown in a closed position;

FIG. 3B is a side view of the fastener of FIG. 3A;

FIG. 3C is an enlarged view of the fastener in an open position;

FIG. 3D is an enlarged view of an alternate configuration of the fastener shown in a closed position;

FIG. 3E is an enlarged view of an alternate configuration of the fastener shown in a closed position;

FIG. 3F is a side view of the fastener of FIG. 3E;

FIG. 3G is an enlarged view of an alternate configuration of the fastener shown in a closed position;

FIG. 4A is a cross-sectional view of a restraining device of the tissue connector assembly of FIG. 1 in a locked position;

FIG. 4B is a cross-sectional view of the restraining device of FIG. 4A taken in the plane including line 4B—4B;

FIG. 4C is a cross-sectional view of the restraining device of FIG. 4A in an unlocked position;

FIG. 5 is an alternate embodiment of the restraining device of FIG. 4A;

FIG. 6 is a perspective of a second embodiment of a tissue connector assembly of the present invention;

FIG. 7 shows two tissue connector assemblies of FIG. 6 in a first step for connecting a graft vessel to a target vessel;

FIG. 8 shows a second step for connecting the graft vessel to the target vessel;

FIG. 9 shows a third step for connecting the graft vessel to the target vessel; and FIG. 10 shows an alternate method for connecting the graft vessel to the target vessel with the tissue connector assemblies of FIG. 6.

Corresponding reference characters indicate corresponding parts throughout the several views of the drawings.

DESCRIPTION OF THE INVENTION

Referring now to the drawings, and first to FIG. 1, a tissue connector assembly constructed according to the principles of the present invention is shown and generally indicated with reference numeral 1. The tissue connector assembly 1 may be used to manipulate and align tissues, or tissue and graft with respect to each other and thereafter connect the tissues together (FIGS. 2A–2C). As used herein, the term graft includes any of the following; homografts, xenografts, allografts, alloplastic materials, and combinations of the foregoing. The tissue connector assembly 1 may be used in vascular surgery to replace or bypass a diseased, occluded, or injured artery by connecting a graft vessel 12 to a coronary artery 14 or vein in an anastomosis, for example. The tissue connector assembly 1 may be used in open surgical procedures or in minimally invasive or endoscopic procedures for attaching tissue located in the chest, abdominal cavity, or retroperitoneal space. These examples, however, are provided for illustration and are not meant to be limiting.

In the embodiment shown in FIG. 1, the tissue connector assembly 1 generally comprises a penetrating member 2, and fastener or surgical clip 10 (FIG. 1). A restraining device, generally indicated at 8 and comprising a spring (or coil) 26 and a locking device generally indicated at 4, is connected to the fastener 10 for holding the fastener in a deformed configuration as farther described below.

The penetrating member or needle 2 has a sharp pointed tip 30 at its distal end for penetrating tissue. The needle 2 may be bent as shown in FIG. 1, for example. The distal end of the needle 2 is preferably rigid to facilitate penetration of tissue. The remaining length of the needle 2 may be rigid or flexible to facilitate movement of the needle through the tissue as further described below. The tip 30 of the needle 2 may be conical, tapered, or grounded to attain a three or four facet tip, for example. The needle 2 may be made from stainless steel or any other suitable material, such as a polymeric material. It is to be understood that the needle 2 may have a shape or radius of curvature other than the one shown, without departing from the scope of the invention. The needle 2 may be integrally formed with the locking device 4 or may be swaged, welded, threadably attached, or attached by any other suitable means to the locking device.

As shown in FIG. 3A, one embodiment of a fastener 10 comprises a deformable wire 34 made of a shape memory alloy. A nickel titanium (nitinol) based alloy may be used, for example. The nitinol may include additional elements which affect the yield strength of the material or the temperature at which particular pseudoelastic or shape transformation characteristics occur. The transformation temperature may be defined as the temperature at which a shape memory alloy finishes transforming from martensite to austenite upon heating (i.e., $A_f$ temperature). The shape memory alloy preferably exhibits pseudoelastic (superelastic) behavior when deformed at a temperature slightly above its transformation temperature. At least a portion of the shape memory alloy is converted from its austenitic phase to its martensitic phase when the wire is in its deformed configuration. As the stress is removed, the material undergoes a martensitic to austenitic conversion and springs back to its original undeformed configuration. When the wire 34 is positioned within the tissue in its undeformed configuration, a residual stress is present to maintain the tissue tightly together (FIG. 2C). In order for the pseudoelastic wire 34 to retain sufficient compression force in its undeformed configuration, the wire should not be stressed past its yield point in its deformed configuration to allow complete recovery of the wire to its undeformed configuration. The shape memory alloy is preferably selected with a transformation temperature suitable for use with a stopped heart condition where cold cardioplegia has been injected for temporary paralysis of the heart tissue (e.g., temperatures as low as 8–10 degrees Celsius).

It is to be understood that the shape memory alloy may also be heat activated, or a combination of heat activation and pseudoelastic properties may be used, as is well known by those skilled in the art.

The cross-sectional diameter of the wire 34 and length of the wire will vary depending on the specific application. The diameter "d" of the wire 34 may be, for example, between 0.001 and 0.015 inch. For coronary bypass applications, the diameter is preferably between 0.001 and 0.008 inch with a diameter "D" of the loop being between 0.0125 and 0.0875 inch (FIG. 3A). The diameter "D" of the loop of the fastener 120 in its closed position is preferably sized to prevent movement between adjacent tissues. As shown in FIG. 3A, the wire 34 has a circular cross-sectional shape. It is to be understood that the wire may have other cross-sectional shapes such as rectangular, or may be formed from multiple strands without departing from the scope of the invention.

The proximal end of the wire 34 may include a stop 36 having a cross-sectional area greater than the cross-sectional area of the wire and coil 26 to prevent the wire and coil from passing through the tissue (FIG. 3C). The stop 36 may be attached to the end of the wire 34 by welding, gluing or other suitable attachment means or may be formed integrally with the wire by deforming the end of the wire. The stop 36 may also be eliminated to facilitate pulling the fastener completely through the tissue, if, for example, the entire fastener needs to be removed from the vessel during the insertion procedure. The distal end of the wire 34 includes an enlarged portion 38 for engagement with the restraining device 8 as further described below (FIG. 4A). The enlarged portion 38 may be formed by deforming the end of the wire 34 by swaging or arc welding, or attaching by welding, swaging, or other suitable means to form an enlarged portion at the end of the wire.

The wire 34 has an undeformed or closed position (state or configuration) (FIG. 3A) for keeping or connecting tissue together, and a deformed or open position (state or configuration) (FIG. 3C) for insertion of the wire into tissue. The wire 34 is preferably not deformed past its yield point in its open position. Accordingly, it may have a U-shaped configuration in its open position to facilitate insertion of the wire 34 through the tissue. It is to be understood that a U-shaped configuration may be alternatively substituted by an equivalent structure such as C-shaped, V-shaped, J-shaped, and other similarly shaped configurations. The wire 34 is moved from its closed position to its open position by the restraining device 8, as further described below. When in its closed position, the wire 34 forms a loop with the ends of the wire in a generally side-by-side or overlapping orientation (FIG. 3B).

The wire 34 may be formed in the above described shape by first wrapping the wire onto a mandrel and heat treating the wire at approximately 400–500 degrees Celsius for approximately 5 to 30 minutes. The wire 34 is then air quenched at room temperature. The mandrel may have a constant diameter or may be conical in shape.

An alternate configuration of the surgical clip 10 in its closed position is shown in FIG. 3D, and generally indicated at 40. The fastener 40 forms a spiral configuration in its closed position for trapping tissue within a loop formed by the spiral. In its open position, the fastener 40 is configured to form less than a fill 360 degree turn.

Another alternate configuration of the surgical clip 10 is shown in FIGS. 3E and 3F in its closed position, and is generally indicated at 41. The fastener 41 is formed in a spiral about a central longitudinal axis A. As shown in FIG. 3F, the fastener 41 has a generally conical shape along the longitudinal axis A, with a decreasing diameter as the radius of curvature of the fastener 41 decreases. The fastener 41 has an inner end portion 45 and an outer end portion 47, with the enlarged portion 38 of the wire being disposed at the outer end portion for engagement with the restraining device 8 (FIG. 3E).

A modification of the fastener is shown in FIG. 3G, and generally indicated at 43. The fastener 43 is same as the fastener 41 described above, except that the enlarged portion 38, which is adapted for engaging a restraining device or releasable mechanism, is positioned at the inner end portion 45 of the fastener. Placement of the restraining device 8 at the inner end portion 45 of the fastener 43 increases the compression force of the wire in its undeformed position on the tissue and decreases the surface area of the fastener exposed to blood flow.

It is to be understood that the fastener 10, 40, 41, 43 may have undeformed or deformed configurations different than those shown herein without departing from the scope of the invention. In addition, a locking clip (not shown) may also be attached to connect the ends of the fastener 10, 40, 41, 43 when the fastener is in its closed position to prevent possible opening of the fastener over time. The locking clip may also be integrally formed with one end of the fastener.

As shown in FIG. 3C, the wire 34 is surrounded by the spring or coil 26 which, along with the locking device 4, restrains the wire in its deformed configuration. The coil 26 comprises a helical wire forming a plurality of loops which define a longitudinal opening 44 for receiving the shape memory alloy wire 34. The coil 26 may be formed from a platinum alloy wire having a cross-sectional diameter of approximately 0.0005–0.005 inch, for example. The wire may have other cross-sectional shapes and be formed of different materials. The coil 26 is preferably sized so that when in its free (uncompressed state) it extends the length of the wire 34 with one end adjacent the stop 36 at the proximal end of the wire and the other end adjacent the enlarged portion 38 at the distal end of the wire (FIG. 3B). It is to be understood that the spring 26 may not extend the full length of the wire. For example, a flange or similar device may be provided on an intermediate portion of the wire 34 to limit movement of the coil along the length of the wire.

When the coil 26 is in its free state (with the wire 34 in its undeformed configuration), loops of the coil are generally spaced from one another and do not exert any significant force on the wire 34 (FIG. 3A). When the coil 26 is compressed (with the wire 34 in its deformed configuration), loops of the coil on the inner portion 46 of the coil are squeezed together with a tight pitch so that the loops are near or contiguous with one another while loops on the outer portion 48 of the coil are spaced from one another (FIG. 3C). This is due to the compressed inner arc length of the coil 26 and the expanded outer arc length of the coil. The compression of the loops on the inner portion 46 of the coil 26 exerts a force on the inner side of the wire 34 which forces the wire to spread open (i.e., tends to straighten the wire from its closed configuration to its open configuration). The end of the coil 26 adjacent the stop 36 is held in a fixed position relative to the wire 34. The opposite end of the coil 26 is free to move along the wire 34 and is held in place when the coil is in its compressed position by the locking device 4 (FIG. 4A).

The locking device 4 shown in FIGS. 1 and 4A–4C comprises a flexible tubular member 50 having a distal end portion 52 coupled to a needle 2 and a proximal end portion 54 releasably attached to the wire 34. The tubular member 50 is movable between a locked position (FIG. 4A) for holding the coil 26 in its compressed position and the wire 34 in its deformed position, and an unlocked position (FIG. 4C) for inserting or releasing the wire and coil. Three slots 58 are formed in the tubular member 50 extending from the proximal end 54 of the member and along at least a portion of the member (FIGS. 4B and 4C). The slots 58 are provided to allow the proximal end 54 of the tubular member 50 to open for insertion and removal of the wire 34 when the tubular member is in its unlocked position (FIG. 4C). It is to be understood that the number of slots 58 and configuration of the slots may vary.

The proximal end 54 of the tubular member 50 includes a bore 62 having a diameter slightly greater than the outer diameter d of the wire 34, but smaller than the diameter of the enlarged portion 38, and smaller than the outer diameter of the coil 26. The bore 62 extends into a cavity 64 sized for receiving the enlarged portion 38 of the wire 34. Member 50 may be described as having an annular flange 61 for releasably securing the enlarged portion 38. As shown in FIG. 4C, upon application of an inwardly directed radial squeezing force on the tubular member 50 the proximal end 54 of the tubular member is opened to allow for insertion or removal of the wire 34. When the force is released (FIG. 4A), the tubular member 50 moves back to its locked position and securely holds the wire 34 in place and compresses the coil 26. A disc 51 may be inserted into the tubular member 50 to act as a fulcrum and cause the proximal end 54 of the tubular member to open upon application of force on the tubular member. Alternatively, the disc 51 may be integrally formed with the tubular member 50. As shown in FIG. 4A, the length l of the bore 62 or flange 61 determines the amount of compression of the coil, which in turn determines the amount of deformation of the wire 34. The greater the length l of the bore 62, the greater the compression of the coil 26 and the more straightening the wire 34 will undergo. The compression of the coil 26 is preferably limited so that the wire 34 is not stressed beyond its yield point. This allows the wire 34 to revert back to its original undeformed configuration and apply sufficient pressure to hold the connected tissue together.

An alternate embodiment of the restraining device is shown in FIG. 5, and generally indicated with reference numeral 70. The restraining device 70 is used with a tubular (hollow) shape memory alloy wire or tube 72 and comprises an elongated member (or mandrel) 74 sized for insertion into the wire. The mandrel 74 is preferably formed from a material which is stiffer than the material of the wire 72 so that upon insertion of the mandrel into the wire, the wire is deformed into its open position. The restraining device 70 includes a stop 76 located at the proximal end of the wire 72. The stop operates to prevent the fastener from being pulled through the tissue, and limits axial movement of the mandrel 74 in the proximal direction (to the right as viewed in FIG. 5). The distal end of the mandrel 74 is releasably attached to the needle 2. It is to be understood that other types of restraining devices may be used without departing from the scope of the invention.

It is to be understood that locking devices other than those described above may be used without departing from the scope of the invention. For example, a locking device (not shown) may comprise a tubular member having an opening formed in a sidewall thereof for receiving an end portion of the wire. The end of the wire may be bent so that it is biased to fit within the opening in the sidewall of the tubular member. An instrument, such as a needle holder may then be used to push the wire away from the opening in the tubular member and release the wire from the tubular member. Various other types of locking devices including a spring detent or bayonet type of device may also be used.

Another embodiment of the tissue connector assembly is shown in FIG. 6 and generally indicated with reference numeral 110. The tissue connector assembly 110 is similar to the tissue connector assembly 1 of the first embodiment, except that a flexible member 118 is inserted between a restraining device 124 and needle 116. FIG. 6 shows the tissue connector assembly 110 with a fastener 120 in an open (deformed) position. The fastener 120 may be the same as the fasteners 10, 40, 41, 43 described above and shown in FIGS. 3A–3G for the tissue connector assembly 1 of the first embodiment, for example. The fastener 120 includes the restraining device 124 comprising a coil 126 and a locking device 128. The locking device 128 is same to the locking device 4 described above and shown in FIGS. 4A–4C, except that the distal end is configured for attachment to the flexible member 118.

The flexible member 118 is attached to the distal end of the locking device 128 with a tapered portion or transition sleeve 156 extending from the locking device to the flexible member 118 to facilitate insertion of the locking device through tissue. The tapered sleeve 156 is preferably sufficiently curved to facilitate movement of the tissue connector assembly 110 through connecting tissue in an anastomosis, for example. The sleeve 156 may be formed from a metal alloy such as stainless steel or a suitable polymeric material. The needle 116 may be swaged into the sleeve 156, or a heat shrink plastic covering may hold the needle in place. The locking device 128 may also be curved.

The flexible member 118 may be in the form of a suture formed from conventional filament material, metal alloy such as nitinol, polymeric material, or any other suitable material. The material may be non-stretchable or stretchable, solid or hollow, and have various cross-sectional diameters. The suture may have a cross-sectional diameter of 0.003 inch, for example. The diameter and length of the suture will vary depending on the specific application. The suture may be attached to the needle 116 by crimping or swaging the needle onto the suture, gluing the suture to the needle, or any other suitable attachment method. The flexible member 118 may have cross-sectional shapes other than the one shown herein.

The needle 116 may be integrally formed with the flexible member 118. The diameter of at least a portion of the needle 116 is preferably greater than the diameter of the flexible member 118 so that the flexible member can easily be pulled through an opening formed in the tissue by the needle.

As noted above, the tissue connector assemblies 1,110 of this invention have many uses They may be especially useful in minimally invasive surgical procedures including creating an anastomosis between a vascular graft 12 and an artery 14 (FIGS. 2A–2C). The anastomosis may be used to replace or bypass a diseased, occluded or injured artery. A coronary bypass graft procedure requires that a source of arterial blood flow be prepared for subsequent bypass connection to a diseased artery. An arterial graft may be used to provide a source of blood flow, or a free graft may be used and connected at the proximal end to a source of blood flow. Preferably, the source of blood flow is one of any number of existing arteries which may be dissected in preparation for the bypass graft procedure. In many instances it is preferred to use the left internal mammary artery (LIMA) or the right internal mammary artery (RIMA), for example. Other vessels which may be used include the saphenous vein, gastroepiploic artery in the abdomen, radial artery, and other arteries harvested from the patient's body as well as synthetic graft materials, such as DACRON® or GORETEX® (expanded polytetrafluoroethylene). If a free graft vessel is used, the upstream end of the dissected vessel, which is the arterial blood source, will be secured to the aorta to provide the desired bypass blood flow, as is well known by those skilled in the art. The downstream end of the graft vessel is trimmed for attachment to an artery, such as the left anterior descending coronary (LAD). It is to be understood that the anastomosis may be formed in other vessels or tissue.

FIGS. 2A–2C and 7–9 show an exemplary use of the tissue connector assemblies 1,110 for connecting a graft vessel 12 to an artery 14 (target vessel). In this example, two tissue connector assemblies 110 (FIG. 6) are used to make connections at generally opposite sides of the graft vessel and a plurality of tissue connector assemblies 1 (FIG. 1) are used to make connections between those made with tissue connector assemblies 110. The procedure may be accomplished with a beating heart procedure with the use of a heart stabilizer to keep the heart stable, for example. The procedure may also be performed endoscopically.

The patient is first prepped for standard cardiac surgery. After exposure and control of the artery 14, occlusion and reperfusion may be performed as required. Referring to FIGS. 7–9, after the arteriotomy of the snared graft vessel 12 has been made to the appropriate length, a tissue connector assembly 110 is attached to the free end of the graft vessel along an edge margin of the vessel. In order to attach the connector assembly 110, the surgeon grasps the needle 116 with a needle holder (e.g., surgical pliers, forceps, or any other suitable instrument) and inserts the needle 116 into an end margin of the graft vessel 12 in a direction from the exterior of the vessel to the interior of the vessel. The surgeon then releases the needle 116 and grasps a forward end of the needle which is now located inside the graft vessel 12 and pulls the needle and a portion of the suture 118 through the vessel. The needle 116 is passed through an opening 121 formed in the sidewall of the artery 14 and inserted into the tissue of the artery in a direction from the interior of the artery to the exterior of the artery. The surgeon then grasps the needle 116 located outside the artery 14 and pulls the needle and a portion of the suture 118 through the arterial wall. A second tissue connector assembly 110 may be inserted at a location generally 180 degrees from the location of the first tissue connector in a conventional "heel and toe" arrangement. Alternatively, a number of tissue connectors 110 may be inserted generally around the location of the heel. The graft vessel 12 may then be pulled towards the artery 14 to determine whether the opening 121 formed in the sidewall of the artery is large enough before completing the anastomosis.

Once the tissue connector assemblies 110 are inserted, the graft vessel 12 is positioned above the opening 121 in the sidewall of the artery 14 (FIG. 7). The fasteners 120 and needles 116 are pulled generally away from the artery 14 to reduce the length of the suture 118 between the vessel 12 and artery and "parachute" the vessel onto the artery (FIG. 8). The needles 116 are then pulled away from the artery 14 until the fastener 120 is positioned within the graft vessel 12 and artery with one end of each fastener extending from the vessel and the opposite end of each fastener extending from the artery (FIG. 9). The edges of the graft vessel 12 and artery 14 are positioned adjacent one another to form a continuous interior and exterior surface along the mating portions of the vessel and artery. As shown in FIG. 2C, the tissue is compressed within the fastener 120.

A surgical instrument (e.g., needle holder) is used to radially squeeze each locking device 128 to release the locking device from the fastener 120. Upon removal of the locking device 128, the coil 126 moves to its free uncompressed state which allows the wire 134 to return to its original undeformed closed position (FIG. 2A). As the wires 134 move to their closed position the adjacent tissues of the graft vessel 12 and artery 14 which were previously pulled together during the parachuting of the graft vessel onto the artery, are squeezed together to securely engage the graft vessel and artery (FIGS. 2B and 2C).

The tissue connector assemblies 1 are subsequently inserted at circumferentially spaced locations around the periphery of the graft vessel 12 to sealingly fasten the graft vessel to the artery 14. The needle 2 of the fastener 1 is inserted into the graft vessel 12 from the exterior surface of the graft vessel and pushed through the graft vessel and artery 14 tissue. The needle holder is then used to pull the needle 2 through the arterial wall. An instrument (same needle holder or other suitable instrument) is used to apply a squeezing force to the locking device 4 to release the wire 34 and coil 26 from the needle 2. This allows the coil 26 to move to its Uncompressed configuration and the wire 34 to move to its closed position. It should be noted that the tissue connector assemblies 110 may remain in their open position while the tissue connector assemblies 1 are inserted into the tissue and moved to their closed position. The locking devices 128 of the tissue connector assemblies 110 may subsequently be removed from the fasteners 120 to allow the fasteners to move to their closed position. The number and combination of tissue connectors assemblies 1,110 required to sealingly secure the connecting tissues together may vary. For example, only tissue connector assemblies 1 may be used to complete the entire anastomosis, or only tissue connector assemblies 110 may be used to connect tissues.

It should be noted that as the locking device 4 is squeezed two steps are accomplished. The fastener 10 is released from the locking device 4, thus allowing the coil 26 to uncompress and the wire 34 to move to its closed configuration, and the needle 2 is released from the fastener. Thus, in the embodiment shown, the locking device 4 provides for simultaneous actuating closure of the fastener 10 and release of the needle 2 from the fastener.

The graft vessel 12 may also be parachuted onto the artery 14 in the method shown in FIG. 10. The needles 116 are inserted into the graft vessel 12 and artery 14 as described above and the sutures 118 are pulled through the vessel so that the fasteners 120 are positioned within the vessel. The needles 116 are then pulled away from the artery 14 to "parachute" the graft vessel 12 onto the artery.

Although the coil 126 is shown as remaining on the wire (FIG. 6), it is to be understood that the coil 126 may also be removed from the wire 134, leaving only the wire in the connected tissue.

Although the suturing procedure has been described for an end-to-side anastomosis, it should be appreciated that the procedure is applicable to an end-to-end and side-to-side anastomosis, connecting various tissue structures including single and multiple tissue structures, and puncture sites, and connecting tissue to a prosthetic graft or valve, for example.

It will be observed from the foregoing that the tissue connector assemblies of the present invention have numerous advantages. Importantly, the assemblies are easier and faster to apply than conventional sutures which require tying multiple knots. The assemblies may be used in minimally invasive procedures including endoscopic procedures, and may be inserted single handedly.

All references cited above are incorporated herein by reference.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. A tissue connector assembly comprising a clip movable between an open configuration and a closed configuration, said clip having a generally U-shaped configuration when in said open configuration, and a mechanical restraining device coupled to said clip for restraining said clip in said open configuration, further comprising a discrete needle coupled to said mechanical restraining device and releasably attached to said clip.

2. The tissue connector assembly of claim 1 wherein at least a portion of said mechanical restraining device remains on said clip when said needle is released from said clip.

3. A tissue connector assembly comprising a clip movable between an open configuration and a closed configuration, said clip having a generally U-shaped configuration when in said open configuration, and a mechanical restraining device releasably coupled to said clip for restraining said clip in said open configuration, wherein said clip comprises a wire, and wherein said wire is tubular.

4. A tissue connector assembly comprising a clip movable between an open configuration and a closed configuration, said clip having a generally U-shaped configuration when in said open configuration, and a mechanical restraining device releasably coupled to said clip for restraining said clip in said open configuration, wherein said clip comprises a wire, and wherein said wire has a first end portion, a second end portion and an elongated member therebetween, said first end portion being coupled to said mechanical restraining device, said second end portion having a cross-sectional area greater than a cross-sectional area of said elongated member.

5. A tissue connector assembly comprising a clip movable between an open configuration and a closed configuration, said clip having a generally U-shaped configuration when in said open configuration, and a mechanical restraining device coupled to said clip for restraining said clip in said open configuration, wherein said clip assumes a spiral configuration in said closed configuration.

6. A tissue connector assembly comprising a clip movable between an open configuration and a closed configuration, said clip having a generally U-shaped configuration when in said open configuration, and a mechanical restraining device releasably coupled to said clip for restraining said clip in said open configuration, wherein said mechanical restraining device comprises a coil surrounding at least a portion of said clip.

7. The tissue connector assembly to claim 6 wherein said coil comprises a plurality of adjacent loops, said coil being compressible with said plurality of adjacent loops being spaced closer to one another along one side of said coil than along an opposite side of said coil.

8. A tissue connector assembly comprising a clip movable between an open configuration and a closed configuration, said clip having a generally U-shaped configuration when in said open configuration, and a mechanical restraining device coupled to said clip for restraining said clip in said open configuration, wherein said mechanical restraining device comprises a coil surrounding at least a portion of said clip, said mechanical restraining device includes a lock releasably engaging said coil, wherein engagement of said lock with said coil biases said clip in said open configuration.

9. A tissue connector assembly comprising a clip movable between an open configuration and a closed configuration, said clip having a generally U-shaped configuration when in said open configuration, and a mechanical restraining device coupled to said clip for restraining said clip in said open configuration, wherein said clip comprises a tubular wire and said mechanical restraining device comprises an elongated member positioned in said wire.

10. A tissue connector assembly comprising a clip adapted to assume an open configuration and a closed configuration and a coil coupled to said clip, wherein said coil is adapted to provide a biasing force to bias said clip in said open configuration, and a needle coupled to said clip.

11. The tissue connector assembly of claim 10 wherein said needle is releasably coupled to said clip.

12. A tissue connector assembly comprising a clip having an open configuration and a closed configuration and a restraint coupled to said clip when in said open configuration, and a discrete needle coupled to said restraint and coupled to said clip.

13. The tissue connector assembly of claim 12 wherein said needle is releasably coupled to said clip.

14. A tissue connector assembly comprising a clip movable between an open configuration and a closed configuration, said clip having a spiral shaped configuration when in said closed configuration, and an open configuration in which said clip is opened from the closed configuration by less than a full 360 degree turn, wherein said clip spirals around a central longitudinal axis when in said closed configuration, said clip having a generally conical shape along said longitudinal axis.

15. The tissue connector assembly of claim 14 wherein said clip has an inner end and an outer end, said inner end having a smaller radius than said outer end, said inner end being coupled to a needle.

16. A tissue connector assembly comprising a clip movable between an open configuration and a closed configuration, said clip having a spiral shaped configuration when in said closed configuration, and an open configuration in which said clip is opened from the closed configuration by less than a full 360 degree turn, and needle releasably attached to said clip.

17. A tissue connector assembly comprising:
   a surgical clip having a relaxed state;
   a needle;
   a connector releasably coupling said needle to said clip; and
   a biasing member associated with said surgical clip;
   wherein said connector, when coupling said needle to said clip, urges said biasing member to bias said clip away from said relaxed state.

18. A tissue connector assembly comprising a needle, a clip, and a locking device releasably connecting said needle to said clip, said locking device being movable between an open position for insertion and removal of said needle and a closed position for coupling said needle to said clip and biasing said clip in open configuration.

19. The tissue connector assembly of claim 18, wherein said clip comprises a wire.

20. The tissue connector assembly of claim 18, further comprising a spring for biasing said clip in said configuration.

21. A tissue connector assembly comprising:
   a surgical clip having a relaxed state;
   a needle;
   a connector releasably coupling said needle to said clip; and
   a biasing member associated with said surgical clip;
   wherein said connector, when coupling said needle to said clip, urges said biasing member to bias said clip away from said relaxed state, wherein said connector comprises a portion forming a recess, and wherein said clip comprises a portion which adapted to mate with said recess.

22. The tissue connector assembly of claim 21, wherein said biasing member comprises a coil surrounding at least a portion of said clip, said coil including a first end restrained from movement in one direction along said clip, and a second movable end, wherein said coupling of said connector with said needle compresses said coil by movement of said second end.

23. A tissue connector assembly comprising a needle, a clip, and a locking device releasably connecting said needle to said clip, said locking device being movable between an open position for insertion and removal of said needle and a closed position for coupling said needle to said clip and biasing said clip in an open configuration, wherein said clip comprises a wire, and wherein said wire comprises shape memory material.

24. Tissue connector apparatus comprising:
   a surgical clip comprising shape memory alloy material and having an undeformed closed configuration and a deformed open configuration; and
   a coil surrounding at least a portion of said clip, said coil urging said clip toward said deformed open configuration when said coil is compressed.

25. The tissue connector apparatus of claim 24 wherein said surgical clip is adapted to connect structures selected from the group consisting of tissue, prostheses, and graft materials.

26. The tissue connector apparatus of claim 24 wherein said surgical clip comprises nitinol.

27. The tissue connector apparatus of claim 24 wherein said clip comprises wire.

28. The tissue connector apparatus of claim 24 wherein said clip comprises nitinol wire.

29. The tissue connector apparatus of claim 24 wherein said clip consists of shape memory alloy wire.

30. The tissue connector apparatus of claim 24 wherein said clip has first and second end portions, further including a coil restraint along the first end portion of said clip for limiting movement of said coil relative to said clip.

31. The tissue connector apparatus of claim 30 wherein said clip has an enlarged portion which forms said coil restraint.

32. The tissue connector apparatus of claim 30 further including a second coil restraint along the second end portion of said clip for limiting relative movement between said coil and said clip.

33. The tissue connector apparatus of claim 32 wherein said restraints each form an enlarged portion on said clip.

34. The tissue connector apparatus of claim 32 wherein said coil has first and second ends, at least one end of said coil ends being slidably movable along said clip.

35. The tissue connector apparatus of claim 32 wherein said undeformed closed configuration is a loop configuration.

36. The tissue connector apparatus of claim 35 wherein said deformed configuration is a U-shaped configuration.

37. Tissue connector apparatus comprising:

a surgical clip comprising shape memory alloy material, said clip having an undeformed closed loop configuration and a deformed open generally U-shaped configuration, said clip further having an enlarged portion; and a coil surrounding at least a portion of said surgical clip and having an end abutting said enlarged portion, said coil urging said clip toward said deformed open configuration when said coil is compressed.

38. The tissue connector apparatus of claim 37 wherein said surgical clip includes a second enlarged portion and said coil is disposed between said enlarged portions.

39. The tissue connector apparatus of claim 38 wherein said surgical clip comprises wire made of shape memory alloy material.

40. Tissue connector apparatus adapted for coupling to a piercing member, said apparatus comprising:

a surgical clip comprising shape memory alloy material and having a closed loop configuration when in a first state and a generally open configuration when in a second state, said clip further having an enlarged portion;

a coil surrounding at least a portion of said clip and having an end abutting said enlarged portion, said coil urging sad clip toward said open configuration when said coil is compressed; and a coupling having a portion releasably coupled to said clip, said coupling portion compressing said coil against said enlarged portion, thereby urging said clip to said open configuration, said coupling having another portion adapted for coupling to said needle for inserting said clip through said structures.

41. The tissue connector assembly of claim 40 wherein said surgical clip has a second enlarged portion that mates with said coupling and forms part of the releasable coupling therewith.

42. A tissue connector assembly for connecting material comprising:

a surgical clip comprising shape memory alloy material, said clip having first and second end portions and an enlarged portion along said first end portion, said clip further being constructed for movement between an open configuration and a closed configuration;

a needle; and a mechanical restraining device coupled to said surgical clip for holding said surgical clip in said open configuration so that it can be inserted trough said material, said mechanical restraining device including a coupling that releasably couples said surgical clip to said needle.

43. A tissue connector assembly of claim 42 wherein said restraining device includes a coil that surrounds at least a portion of said clip, said coil being compressed between said coupling and said clip enlarged portion and urging said surgical clip toward said open configuration.

44. The tissue connector assembly of claim 43 wherein said surgical clip includes a second enlarged portion that is releasably coupled to said coupling.

45. The tissue connector assembly of claim 44 wherein said coil is disposed between said enlarged portions.

46. The tissue connector assembly of claim 43 wherein said coil has first and second ends, said first end abutting the enlarged portion that is along said first end portion of said clip and said coil second end abutting said coupling.

47. A tissue connector assembly for connecting at least two structures together, said assembly comprising a surgical clip, which is adapted to connect the at least two structures together, a needle, which is adapted to penetrate said structures, and a coupling, said surgical clip having first and second ends and being constructed for movement between an open configuration for insertion into said structures and a closed configuration for holding said structures together, said coupling having one portion releasably coupled to the first end of said surgical clip and a second portion coupled to said needle.

48. The tissue connector assembly of claim 47 wherein said clip as an enlarged portion, and further including a coil surrounding at least a portion of said clip and being compressed between said coupling and said enlarged portion.

* * * * *